(12) United States Patent
Rand

(10) Patent No.: US 6,575,162 B1
(45) Date of Patent: Jun. 10, 2003

(54) INHALATION DEVICE

(75) Inventor: Paul Kenneth Rand, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/806,042

(22) PCT Filed: Sep. 23, 1999

(86) PCT No.: PCT/EP99/07079

§ 371 (c)(1),
(2), (4) Date: Mar. 26, 2001

(87) PCT Pub. No.: WO00/18457

PCT Pub. Date: Apr. 6, 2000

(30) Foreign Application Priority Data

Sep. 26, 1998 (GB) .............................................. 9820886

(51) Int. Cl.[7] .............................................. A61M 15/00
(52) U.S. Cl. .............................. 128/203.15; 128/200.23
(58) Field of Search ................. 128/200.14, 200.18, 128/200.21–200.23, 203.12, 203.14, 203.15, 203.21, 205.23, 200.11, 200.24; 604/58

(56) References Cited

U.S. PATENT DOCUMENTS

| | | | | |
|---|---|---|---|---|
| 3,151,618 A | * | 10/1964 | Wakeman | 128/200.23 |
| 3,191,867 A | * | 6/1965 | Helms | 239/288.5 |
| 3,622,053 A | | 11/1971 | Ryden | |
| 3,739,950 A | * | 6/1973 | Gorman | 222/182 |
| 4,114,811 A | * | 9/1978 | Loeffler | 128/200.23 |
| 4,130,116 A | | 12/1978 | Cavazza | |
| 4,637,528 A | * | 1/1987 | Wachinski et al. | 222/182 |
| 5,082,148 A | * | 1/1992 | Dunning | 128/203.15 |
| 5,284,133 A | * | 2/1994 | Burns et al. | 128/200.14 |
| 5,347,998 A | | 9/1994 | Hodson et al. | |
| 5,447,151 A | * | 9/1995 | Bruna et al. | 128/203.15 |
| 5,505,194 A | * | 4/1996 | Adjei et al. | 128/200.23 |
| 5,921,237 A | * | 7/1999 | Eisele et al. | 128/203.21 |
| 6,158,431 A | * | 12/2000 | Poole | 128/200.16 |
| 6,182,655 B1 | * | 2/2001 | Keller et al. | 128/203.12 |
| 6,223,746 B1 | * | 5/2001 | Jewett et al. | 128/200.14 |
| 6,260,549 B1 | * | 7/2001 | Sosiak | 128/200.14 |
| 6,273,084 B1 | * | 8/2001 | Frid | 128/200.23 |
| 6,422,236 B1 | * | 7/2002 | Nilsson et al. | 128/203.15 |

FOREIGN PATENT DOCUMENTS

| | | | | |
|---|---|---|---|---|
| EP | 0028929 | 5/1981 | | |
| GB | 2063075 | 6/1981 | | |
| GB | 2074454 | 11/1981 | | |
| WO | 9211051 | 7/1992 | | |
| WO | WO 93/09831 | * | 5/1993 | 128/203.15 |
| WO | WO 94/21317 | * | 9/1994 | 128/203.15 |
| WO | 9940959 | 8/1999 | | |

* cited by examiner

Primary Examiner—Weilun Lo
Assistant Examiner—Teena Mitchell
(74) Attorney, Agent, or Firm—James P. Riek

(57) ABSTRACT

There is provided an inhalation device suitable for dispensing medicament, particularly medicament for use in the treatment of respiratory disorders. The device comprises a body; a medicament carrier, locatable within said body; a mouthpiece, reversibly movable from a storage position wherein said mouthpiece is within the body to an in-use position wherein a portion of the mouthpiece protrudes from the body and wherein the mouthpiece is in communication with the medicament carrier to allow passage of medicament therebetween; and a mouthpiece actuator, slidably movable relative to the body, and coupled to the mouthpiece such that movement of the mouthpiece actuator in a first direction moves the mouthpiece towards said storage position and movement of the mouthpiece actuator in an opposing direction moves the mouthpiece towards the in-use position.

49 Claims, 5 Drawing Sheets

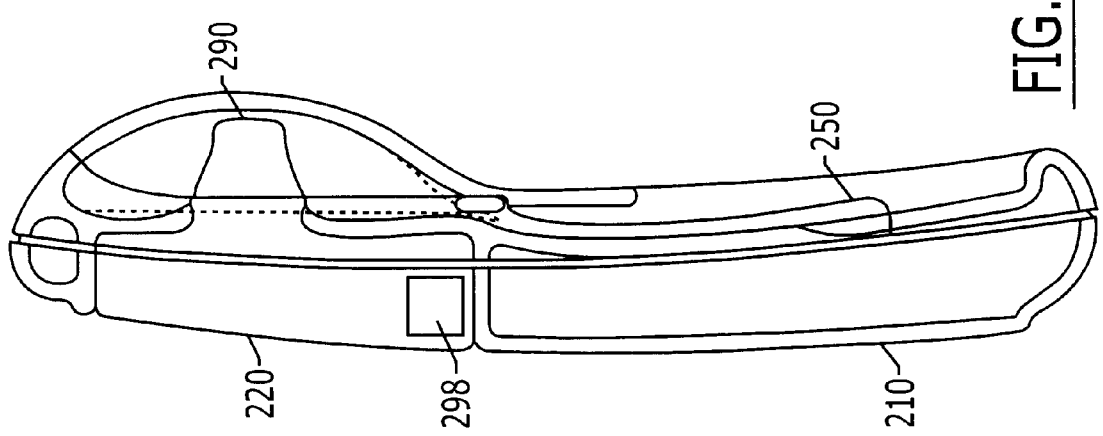
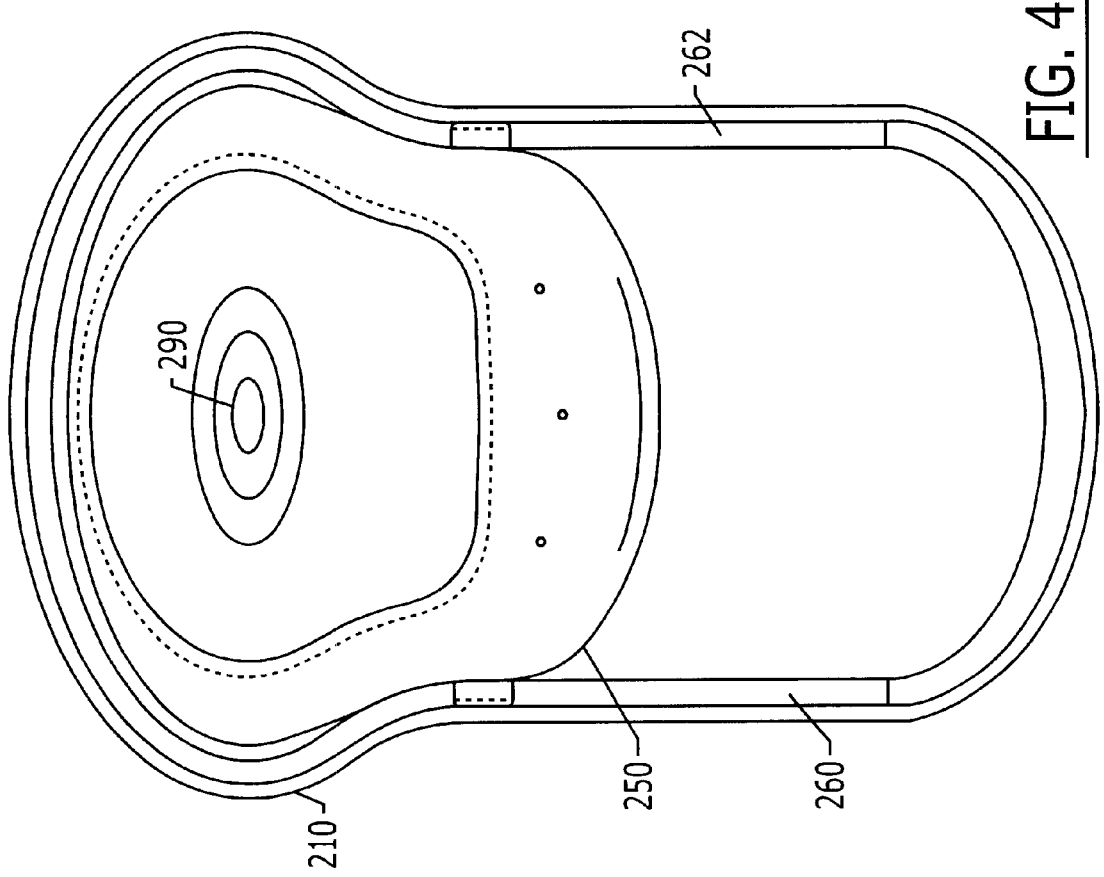

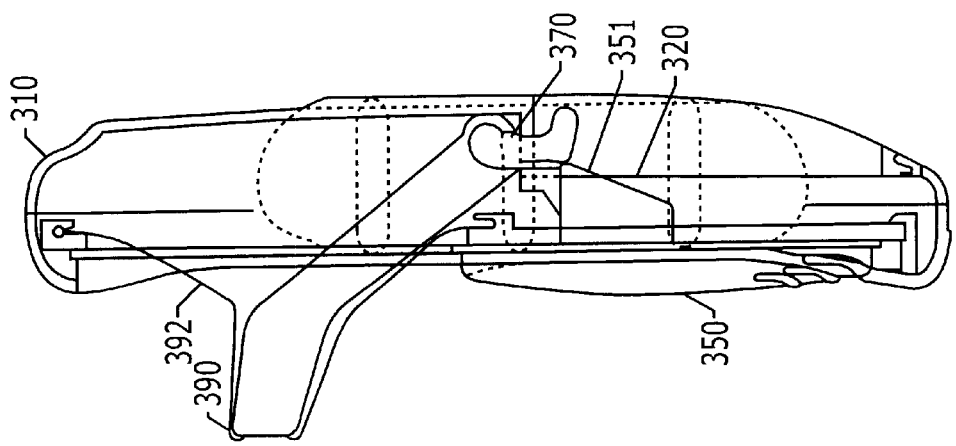
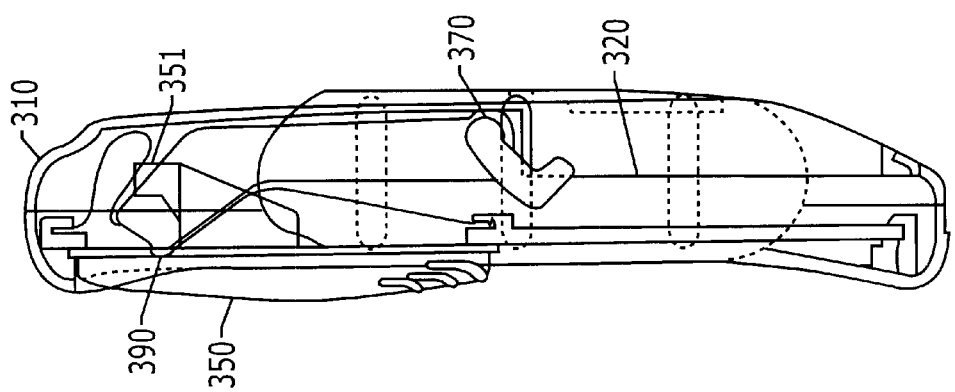
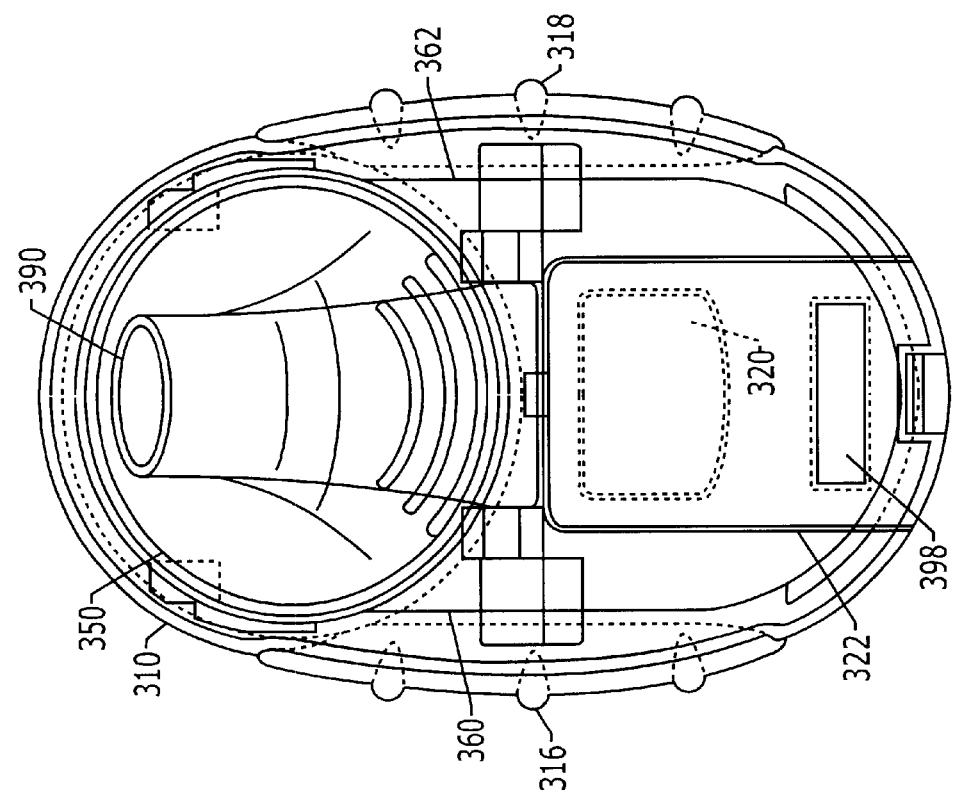

INHALATION DEVICE

CROSS REFERENCE TO RELATED APPLICATIONS

This application is filed pursuant to 35 U.S.C. §371 as a U.S. National Phase Application of International Application No. PCT/EP99/07079 filed Sep. 23, 1999, which claims priority from GB9820886.1 filed Sep. 26, 1998.

The present invention relates to an inhalation device for use in the administration of medicament to a patient. The device has a mouthpiece, which is reversibly retractable from a storage position located inside the body of the device to a dispensing position in which the mouthpiece protrudes from the body of the device.

BACKGROUND OF THE INVENTION

The use of inhalation devices in the administration of medicaments, for example in bronchodilation therapy, is well known. Such devices generally comprise a body or housing within which a medicament container is located. A mouthpiece (or nozzle) is typically provided, wherein 'in use' the mouthpiece communicates with the medicament container to allow passage of medicament from the source to the mouthpiece and thence, to the patient.

In a typical dispensing operation the body of the device is held by the patient and the mouthpiece (or nozzle) of the inhalation device is placed in the mouth (or nose) of the patient. The patient inhales, thereby causing transfer of medicament from the medicament container to the interior of the body of the patient.

When not in use it is desirable, from a hygiene standpoint, that the mouthpiece is provided with some kind of protective cover. The cover desirably acts both to prevent build-up of dirt on the mouthpiece and to prevent ingress of dirt into the body of the device through the mouthpiece, which might then be subject to inhalation by a patient.

It is known to provide the mouthpiece with a protective cap which acts as a protective cover. The cap may either be an entirely separate element or it may be joined to the body of the device in some way. DE-A-3,639,836, for example, describes a device in which the protective cap is mounted on an arm, which is pivotally mounted to the body of the device.

As an alternative to the use of a protective cap, one might envisage a device having a mouthpiece which is reversibly retractable from a storage position in which the mouthpiece is contained within the body of the device to a dispensing position in which the mouthpiece protrudes from the body of the device. In a device of this type the body of the device itself acts as the protective cover when the mouthpiece is in the storage position. The mouthpiece cover is thus an integral part of the inhalation device, avoiding contamination problems of prior art inhalation devices caused by the loss of removable mouthpiece covers.

GB-A-2,074,454 describes an inhalation device comprising a tubular body adapted for detachable fitting to an aerosol container. A mouthpiece is provided, which is movable from a storage position to a dispensing position by means of a cap, rotatably mounted on the tubular body, which has actuating means associated therewith. The cap and tubular body are provided with openings of similar dimensions. Manual rotation of the cap to bring the openings into register causes the actuating means to move the mouthpiece to the dispensing position in which the mouthpiece protrudes from the body of the device. Conversely, rotation of the cap by the user to bring the openings out of register causes the mouthpiece to be moved to the storage position in which the mouthpiece is contained within the body of the device.

For the convenience of the user, it is desirable that the inhalation device is arranged to allow movement of the mouthpiece from the storage to dispensing position (and vice-versa) by a non-complex, preferably one-handed operation. The device described in GB-A-2,074,454 is complex to actuate, and in particular would be very difficult to actuate by means of a one-handed operation, since it requires a rotatory movement of the cap relative to the body. This would normally require the user to hold the body in one hand, the cap in another and thence, to perform the required relative rotatory movement.

The Applicants have now found that actuation of the mouthpiece can be facilitated if the movement of the mouthpiece is achieved through the use of a mouthpiece actuator, which is slidably movable relative to the body of the device. One handed operation is thus, for example, achievable if the user holds the body of the device in the palm of a partially cupped hand and employs the thumb to provide sliding movement to the mouthpiece actuator, thereby causing movement of the mouthpiece.

BRIEF SUMMARY OF THE INVENTION

According to one aspect of the present invention there is provided an inhalation device for dispensing medicament comprising a body;

a medicament carrier;

a mouthpiece, reversibly movable from a storage position wherein said mouthpiece is within said body to an in use position wherein a portion of the mouthpiece protrudes from the body and wherein the mouthpiece is in communication with said medicament carrier to allow passage of medicament therebetween; and a mouthpiece actuator, slidably movable relative to the body, and coupled to the mouthpiece such that user movement of said mouthpiece actuator in a first direction moves the mouthpiece towards said storage position and user movement of the mouthpiece actuator in an opposing direction moves the mouthpiece towards said in-use position.

Herein the term 'mouthpiece' is used in a generic sense to mean an element shaped such as to be insertable into the mouth or nose of a patient for inhalation therethrough.

In one preferred aspect, the mouthpiece actuator and mouthpiece are coupled by a coupling mechanism. In one particularly preferred aspect, the coupling mechanism comprises a rack and pinion mechanism. In another particularly preferred aspect, the coupling mechanism comprises a hinged lever mechanism.

In one aspect the medicament carrier is within the body. In another aspect the medicament carrier is attachable to the exterior of the body.

In another preferred aspect, the mouthpiece actuator and mouthpiece are directly coupled.

Preferably, the mouthpiece is comprised of an elastic material.

Preferably, the mouthpiece is provided with a cover comprised of an elastic material.

Preferably, the inhalation device additionally comprises a curtain arrangement contactable by the mouthpiece on movement of the mouthpiece from the storage to the in-use position. More preferably, the curtain arrangement comprises a plurality of curtains comprised of an elastomeric material.

Preferably, the mouthpiece actuator is provided with a safety trigger mechanism to prevent accidental actuation thereof.

Preferably, at least a portion of the mouthpiece actuator is shaped for ease of grip by the user.

Preferably, at least a portion of the mouthpiece actuator has a friction-enhancing coating.

Preferably, the device is provided with a dose counter, which indicates the number of doses dispensed from or remaining in the container. More preferably, the dose counter comprises an indexing mechanism actuated by a predetermined movement of the medicament container relative to the body.

Preferably, the mouthpiece is actuable by a sliding thumb motion.

Preferably, the medicament container is an aerosol or a dry-powder container.

According to another aspect of the present invention, there is provided the use of an inhalation device provided herein for dispensing medicament.

Preferred embodiments of the inhalation device according to the present invention will now be described with reference to the accompanying drawings in which:

BRIEF DESCRIPTION OF THE SEVERAL VIEWS OF THE DRAWINGS

FIG. 4 is a sectional plan view of a third inhalation device in accord with the present invention;

FIG. 5 is a sectional side view of the device of FIG. 5;

FIG. 6 is a sectional plan view of a fourth inhalation device in accord with the present invention;

FIG. 7a is a sectional side view of the device of FIG. 6 wherein the mouthpiece is in the storage position;

FIG. 7b is a sectional side view of the device of FIG. 6 and FIG. 7a wherein the mouthpiece is in the in-use position.

DETAILED DESCRIPTION

Figure 1:
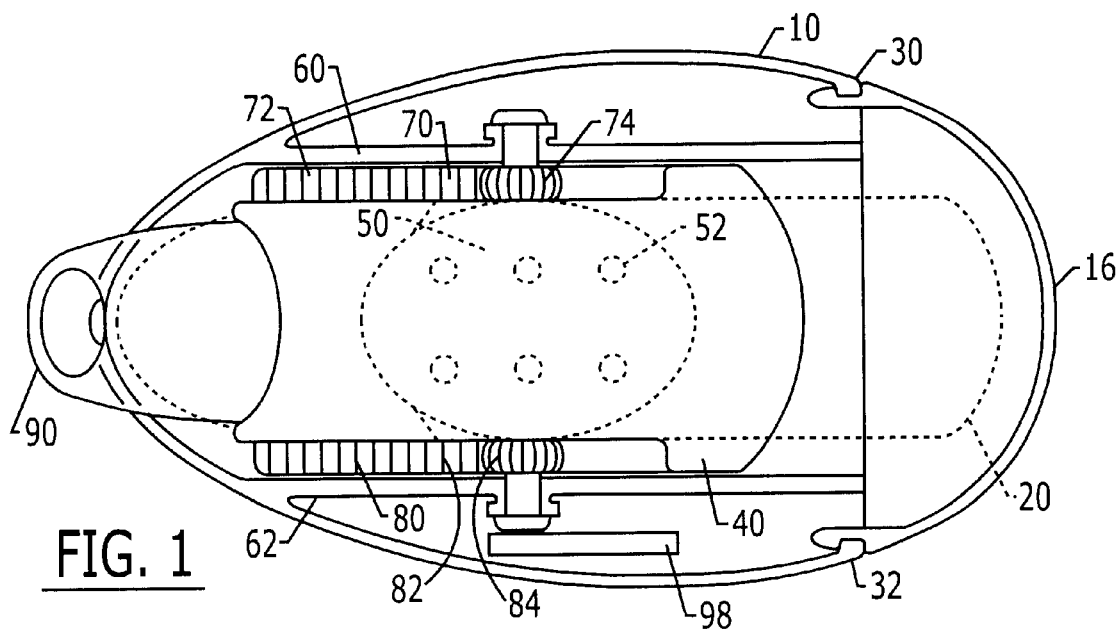
FIG. 1 is a sectional plan view of a first inhalation device in accord with the present invention.
Figure 2A:
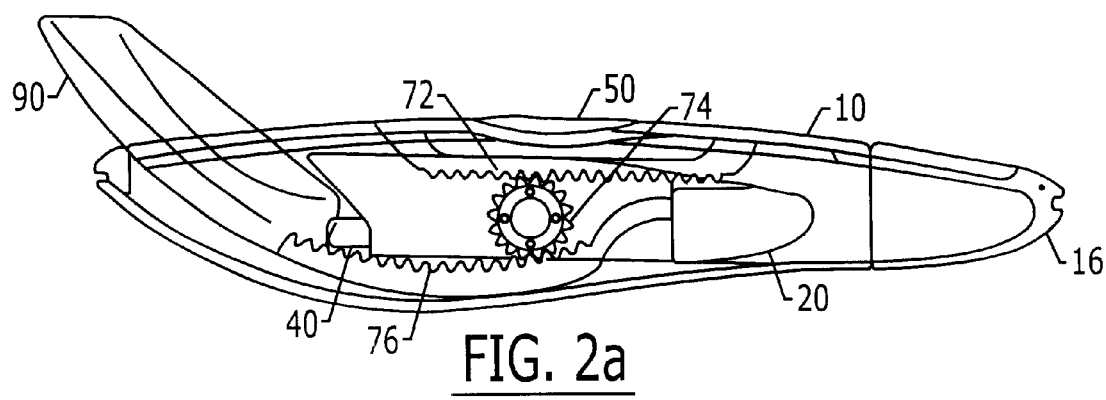
FIG. 2a is a sectional side view of the device of FIG. 1, wherein the mouthpiece is in the in-use position.
Figure 2B:
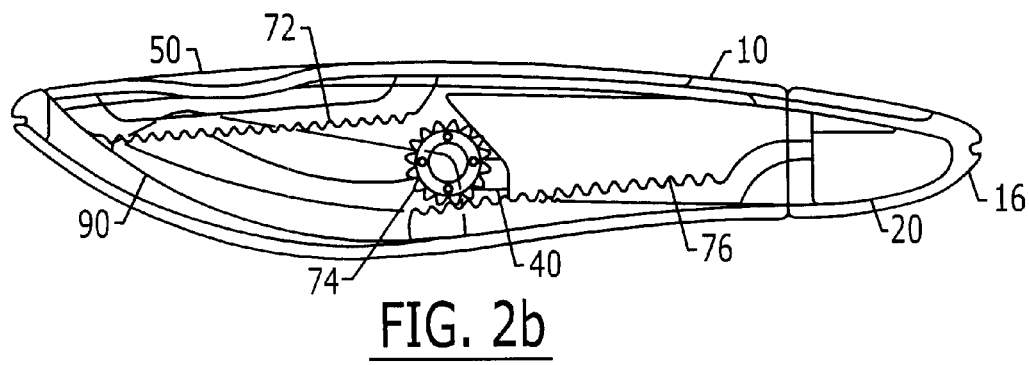
FIG. 2b is a sectional side view of the device of FIG. 1, wherein the mouthpiece is in the storage position.

FIGS. 1, 2a and 2b show a first inhalation device herein comprising a body 10 having an end cap 16, wherein the end cap 16 is reversibly attached to the body 10 by a snap fit mechanism 30, 32. Within the body there is provided a medicament container 20, which is in communication with a hollow transition piece 40 also provided in said body 10.

An essentially flat cover 50 is retainably mounted on first and second guide rails 60, 62 provided on a first face of the body 10 for slidable movement thereon. The exterior surface of the cover 50 has contours 52 for ease of grip by the user. The interior surface of the cover 50 communicates with first and second rack pinion mechanisms 70, 80 which are aligned with the axes defined by the first and second guide rails 60, 62. Each of the first and second rack and pinion mechanisms 70, 80 (wherein, for clarity, only the first mechanism is shown in detail on FIGS. 2a and 2b) comprises a first rack 72, 82 attached to the cover 50, which communicates with a wheel 74, 84 axially mounted to the body 10, which wheel 74, 84 communicates with a curved second rack 76 which is mounted for communication with the mouthpiece 90.

Actuation of the device from the storage position (shown in FIG. 2b) to the in-use position) (shown in FIGS. 1 and 2a) is achievable by the user sliding the cover 50 along the guide rails 60, 62 in a direction towards the end cap 16. The first rack 72 is thus bought into engagement with wheel 74, which rotates and engages second rack 76, thereby moving the second rack 76 in the opposite direction. In turn, the movement of the second rack 76 causes the mouthpiece 90 to be moved to the in-use position, in which it protrudes from the body 10. In the in-use position it may be seen that the interior of the mouthpiece 90 communicates with the hollow interior of the transition piece 40, which itself communicates with the medicament container 20. Thus an inhalation passageway is provided from the mouthpiece 90 to the medicament container 20. Deactivation is achievable by the reverse sliding motion of the cover 50.

Figure 3A:
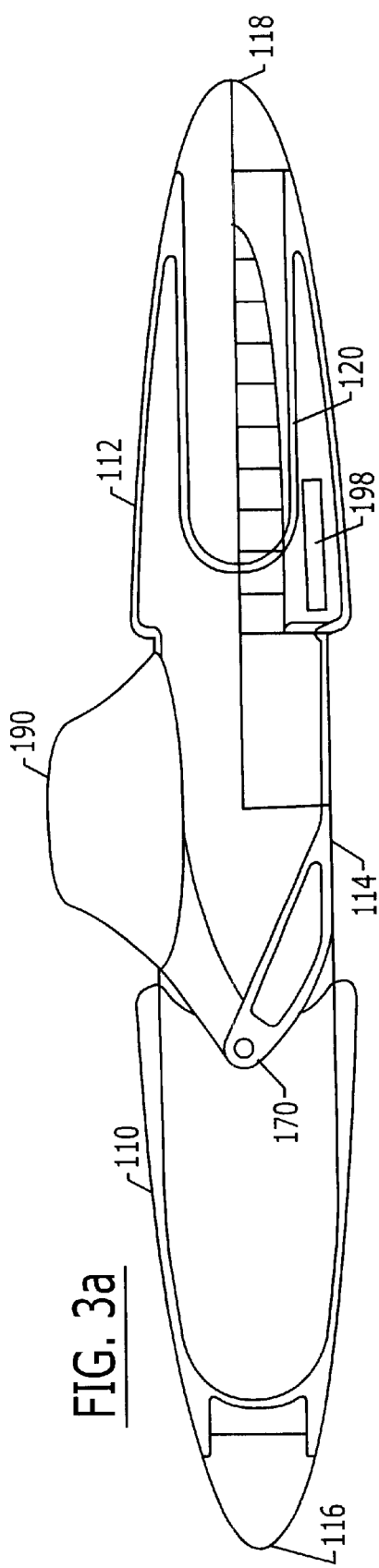
FIG. 3a is a sectional side view of a second inhalation device in accord with the present invention wherein the mouthpiece is in the storage position.
Figure 3B:
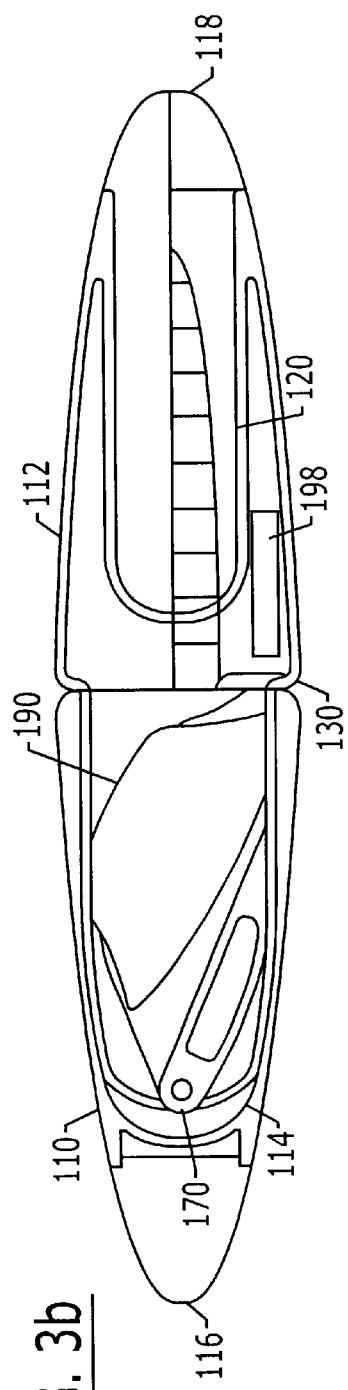
FIG. 3b is a sectional side view of the device of FIG. 3a wherein the mouthpiece is in the storage position.
Figure 8:
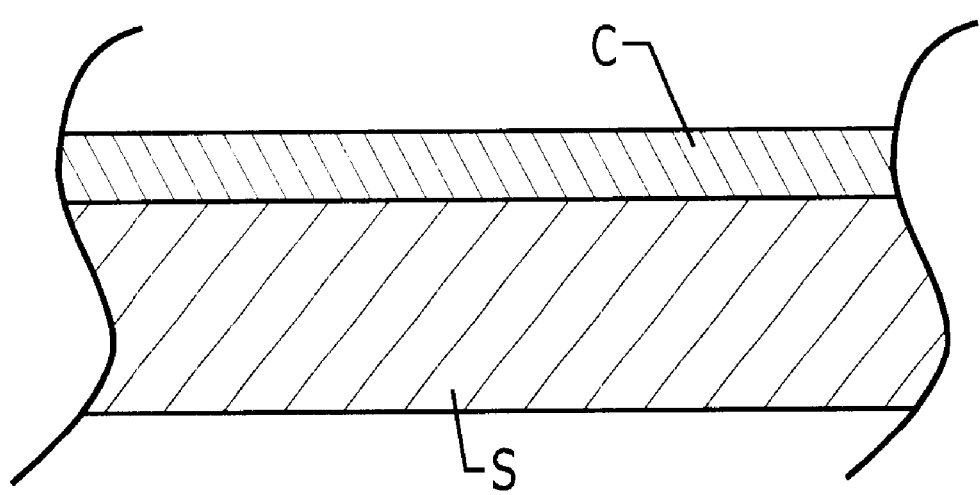
FIG. 8 is a cross sectional view of a section mouthpiece actuator having surface (S) with an optional coating layer (C) thereon.

FIGS. 3a and 3b show a second inhalation device herein having a flattened cigar shaped body comprising first 110 and second 112 body segments, wherein a male portion 114 of the second body segment 112 is slidably receivable within the interior of the first body segment 110, to form the full body-shape. When so received, the two body segments are releasably secured to each other by snap-lock mechanism 130. The first and second segments 110, 112 are provided with end caps 116, 118, which are coated with an elastomeric material for ease of grip thereof. A medicament cartridge 120 is provided within the second body segment 112. Mouthpiece 190 is coupled to the second body segment 112 through hinged arm mechanism 170.

Actuation of the device from the storage position shown in (FIG. 3b) to the in-use position (shown in FIG. 3a) is achievable by the user releasing the snap-lock 130 and slidably separating the first and second body segments 110, 112 away from each other. The movement of the second body segment 112 is translated to the mouthpiece 190 through the coupling provided by the hinged arm mechanism such that the mouthpiece 190 is moved to the in-use position. Deactivation is achievable by sliding the first and second body segments 110, 112 towards each other until the snap-lock 130 snaps into action.

FIGS. 4 and 5 show a third inhalation device herein comprising a body 210, which is overall shaped for ease of grip in the hand of a user. Within the body 210 there is provided a medicament cartridge 220 and attached thereto mouthpiece 290, wherein the mouthpiece is comprised of a resiliently deformable elastomeric material. A shaped cover 250 is retainably mounted on first and second guide rails 260, 262 provided on the body 210 for slidable movement thereon.

Actuation of the device from the storage position (shown in FIG. 4) to the in-use position (shown in FIG. 5) is achievable by the user sliding the cover 250 along the guide rails 260, 262 (e.g. by a thumb movement), thereby revealing the mouthpiece 290, which 'pops out' into its characteristic shape. Deactivation is achievable by the reverse sliding action, which causes deformation of the mouthpiece 290.

FIGS. 6, 7a and 7b show a fourth inhalation device herein comprising a body 310 provided with a medicament compartment 320 which is accessible for loading of medicament by opening of door 322. Contoured elastomeric strips 316, 318 are provided to the body 310 for ease of grip thereof.

A circular, essentially flat cover 350 is retainably mounted on the first and second guide rails 360, 362 provided on the body 310. The interior surface of the cover 350 is coupled through articulated assembly 370 to mouthpiece 390, which is itself hingedly mounted. Cover 350 comprises an angled portion 351. The mouthpiece 390 is provided with a thin, flexible elastomeric covering 392 to form a curtain arrangement covering the mouthpiece 390, which is contactable by the mouthpiece on movement of the mouthpiece from the storage to the in-use position. More preferably, the curtain arrangement comprises a plurality of curtains or coverings 392.

Actuation of the device from the storage position (shown in FIGS. 6 and 7a) to the in-use position (shown in FIG. 7b) is achievable by the user slidably moving the cover 350 along the guide rails 360, 362. Movement of the cover to said in-use position causes said angled portion 351 to contact said articulated assembly 370. The sliding action is coupled via articulated assembly 370 to the mouthpiece 390, which is moved to a position in which it stands proud from the body 310, and in which there is an inhalation passageway established between the mouthpiece 390 and the medicament compartment 320. Deactivation is achievable by performance of the reverse sliding action.

Optionally, the device may be provided with a dose counter (98, 198, 298 and 398), which indicates the number of doses dispensed from or remaining in the container. More preferably, the dose counter comprises an indexing mechanism actuated by a predetermined movement of the medicament container relative to the body.

The inhalation device herein is suitable for dispensing medicament, particularly for the treatment of respiratory disorders. Appropriate medicaments may thus be selected from, for example, analgesics, e.g. codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti- inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl)ethoxy] hexyl]methyl] benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

What is claimed is:

1. An inhalation device for dispensing medicament comprising a body;

a medicament carrier;

a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and a mouthpiece actuator, slidably movable relative to the body, and coupled to the mouthpiece such that user movement of said mouthpiece actuator in a first direction moves the mouthpiece towards said storage position and user movement of the mouthpiece actuator in an opposing direction moves the mouthpiece towards said in-use position, without increasing the length of the body of the inhalation device, and said mouthpiece actuator and mouthpiece are coupled by a rack and pinion mechanism.

2. An inhalation device according to claim 1, wherein the medicament carrier is within the body.

3. An inhalation device according to claim 1, wherein the medicament carrier is attachable to the exterior of the body.

4. An inhalation device according to claim 1, wherein the mouthpiece is provided with a cover comprised of an elastic material.

5. An inhalation device according to claim 1, wherein at least a portion of the mouthpiece actuator is shaped for ease of grip by the user.

6. An inhalation device according to claim 1, wherein at least a portion of the mouthpiece actuator comprises a friction-enhancing coating material.

7. An inhalation device according to claim 1, wherein the medicament container contains medicament in an aerosol formulation.

8. An inhalation device according to claim 1, wherein the medicament container contains a medicament in dry-powder form.

9. An inhalation device according to claim 1, wherein the device is provided with a dose counter.

10. An inhalation device according to claim 9, wherein the dose counter comprises an indexing mechanism actuated by a predetermined movement of the medicament container relative to the body.

11. An inhalation device according to claim 1, actuable by a sliding thumb motion.

12. Use of an inhalation device according to claim 1 for dispensing medicament.

13. An inhalation device for dispensing medicament comprising
a body;
a medicament carrier;
a mouthpiece, reversibly movable from a storage position wherein said mouthpiece is within said body to an in-use position wherein a portion of the mouthpiece protrudes from the body and wherein the mouthpiece is in communication with said me dicament carrier to allow passage of medicament therebetween; and
a mouthpiece actuator, slidably movable relative to the body, and coupled to the mouthpiece such that user movement of said mouthpiece actuator in a first direction moves the mouthpiece towards said storage position and user movement of the mouthpiece actuator in an opposing direction moves the mouthpiece towards said in-use position, without increasing the length of the body of the inhalation device, and
wherein the mouthpiece actuator and mouthpiece are directly coupled, and force exerted by said mouthpiece actuator upon mouthpiece causes said mouthpiece to move to the in-use position.

14. An inhalation device according to claim 13, wherein said mouthpiece actuator comprises an angled portion, and said mouthpiece comprises an articulated assembly, wherein movement of the mouthpiece actuator to said in-use position causes said angled portion to contact said articulated assembly causing said mouthpiece to stand proud from said the body.

15. An inhalation device according to claim 13, wherein the medicament carrier is within the body.

16. An inhalation device according to claim 13, wherein the medicament carrier is attachable to the exterior of the body.

17. An inhalation device according to claim 13, wherein the mouthpiece is provided with a cover comprised of an elastic material.

18. An inhalation device according to claim 13, wherein at least a portion of the mouthpiece actuator is shaped for ease of grip by the user.

19. An inhalation device according to claim 13, wherein at least a portion of the mouthpiece actuator comprises a friction-enhancing coating material.

20. An inhalation device according to claim 13, wherein the medicament container contains medicament in an aerosol formulation.

21. An inhalation device according to claim 13, wherein the medicament container contains a medicament in dry-powder form.

22. An inhalation device according to claim 13, wherein the device is provided with a dose counter.

23. An inhalation device according to claim 22 wherein the dose counter comprises an indexing mechanism actuated by a predetermined movement of the medicament container relative to the body.

24. An inhalation device according to claim 13, actuable by a sliding thumb motion.

25. Use of an inhalation device according to claim 13 for dispensing medicament.

26. An inhalation device for dispensing medicament comprising
a body;
a medicament carrier;
a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and
a mouthpiece actuator, slidably movable relative to the body, and coupled to the mouthpiece such that user movement of said mouthpiece actuator in a first direction moves the mouthpiece towards said storage position and user movement of the mouthpiece actuator in an opposing direction moves the mouthpiece towards said in-use position, and
wherein the mouthpiece is comprised of a resiliently deformable elastic material, wherein said mouthpiece is deformed within said housing when in said storage position, and automatically expands to a non-deformed form when in said in-use position.

27. An inhalation device according to claim 26, wherein the medicament carrier is within the body.

28. An inhalation device according to claim 26, wherein the medicament carrier is attachable to the exterior of the body.

29. An inhalation device according to claim 26, wherein the mouthpiece is provided with a cover comprised of an elastic material.

30. An inhalation device according to claim 26, wherein at least a portion of the mouthpiece actuator is shaped for ease of grip by the user.

31. An inhalation device according to claim 26, wherein at least a portion of the mouthpiece actuator comprises a friction-enhancing coating material.

32. An inhalation device according to claim 26, wherein the medicament container contains medicament in an aerosol formulation.

33. An inhalation device according to claim 26, wherein the medicament container contains a medicament in dry-powder form.

34. An inhalation device according to claim 26, wherein the device is provided with a dose counter.

35. An inhalation device according to claim 34 wherein the dose counter comprises an indexing mechanism actuated by a predetermined movement of the medicament container relative to the body.

36. An inhalation device according to claim 26, actuable by a sliding thumb motion.

37. Use of an inhalation device according to claim 26 for dispensing medicament.

38. An inhalation device for dispensing medicament comprising
a body;
a medicament carrier;
a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and
a mouthpiece actuator, slidably movable relative to the body, and coupled to the mouthpiece such that movement of said mouthpiece actuator in a first direction moves the mouthpiece towards said storage position and movement of the mouthpiece actuator in an opposing direction moves the mouthpiece towards said in-use position, and
a curtain arrangement, comprising one or more flexible coverings, said coverings, contactable by the mouthpiece on movement of the mouthpiece from the storage to the in-use position.

39. An inhalation device according to claim 38, wherein said curtain arrangement comprises an elastomeric material.

40. An inhalation device according to claim 38, wherein the medicament carrier is within the body.

41. An inhalation device according to claim 38, wherein the medicament carrier is attachable to the exterior of the body.

42. An inhalation device according to claim 38, wherein at least a portion of the mouthpiece actuator is shaped for ease of grip by the user.

43. An inhalation device according to claim 38, wherein at least a portion of the mouthpiece actuator comprises a friction-enhancing coating material.

44. An inhalation device according to claim 38, wherein the medicament container contains medicament in an aerosol formulation.

45. An inhalation device according to claim 38, wherein the medicament container contains a medicament in dry-powder form.

46. An inhalation device according to claim 38, wherein the device is provided with a dose counter.

47. An inhalation device according to claim 46, wherein the dose counter comprises an indexing mechanism actuated by a predetermined movement of the medicament container relative to the body.

48. An inhalation device according to claim 38, actuable by a sliding thumb motion.

49. Use of an inhalation device according to claim 38 for dispensing medicament.

* * * * *